(12) United States Patent
Merendino, Sr.

(10) Patent No.: US 7,543,506 B2
(45) Date of Patent: Jun. 9, 2009

(54) ELECTROMAGNETIC ROTATION AND STABILITY APPARATUS

(75) Inventor: Paul A. Merendino, Sr., Mogadore, OH (US)

(73) Assignee: Bridgestone Firestone North American Tire, LLC, Nashville, TN (US)

( * ) Notice: Subject to any disclaimer, the term of this patent is extended or adjusted under 35 U.S.C. 154(b) by 85 days.

(21) Appl. No.: 11/685,412

(22) Filed: Mar. 13, 2007

(65) Prior Publication Data

US 2008/0223145 A1    Sep. 18, 2008

(51) Int. Cl.
    *G01B 7/16* (2006.01)
(52) U.S. Cl. ......................... 73/779; 73/777
(58) Field of Classification Search ............... 73/779, 73/777
    See application file for complete search history.

(56) References Cited

U.S. PATENT DOCUMENTS

| | | | |
|---|---|---|---|
| 2,075,968 A | 4/1937 | Von Heydekampf | |
| 3,492,566 A | 1/1970 | Gross | |
| 3,575,045 A | 4/1971 | Knights | |
| 3,609,526 A | 9/1971 | Chaberski | |
| 3,675,475 A | 7/1972 | Weinstein | |
| 3,696,664 A | 10/1972 | Moser et al. | |
| 3,746,937 A | 7/1973 | Koike | |
| 3,854,328 A | 12/1974 | Schmidt | |
| 4,391,087 A | 7/1983 | Greive et al. | |
| 4,478,086 A | 10/1984 | Gram | |
| 4,603,588 A | 8/1986 | Niermann et al. | |
| 4,836,029 A | 6/1989 | Skala et al. | |
| 4,869,112 A | 9/1989 | Gram et al. | |
| 4,896,339 A | 1/1990 | Fukumoto | |
| 4,998,441 A | 3/1991 | Stuart | |
| 5,005,424 A | 4/1991 | Markowski | |
| 5,095,757 A | 3/1992 | Larsen et al. | |
| 5,361,640 A | 11/1994 | Carroll et al. | |
| 5,425,276 A | 6/1995 | Gram et al. | |
| 5,448,168 A | 9/1995 | Hirano et al. | |
| 5,535,853 A | 7/1996 | Skalski | |
| 5,572,079 A * | 11/1996 | Pinkerton | 310/90.5 |
| 5,693,890 A | 12/1997 | Holmes | |
| 5,719,339 A | 2/1998 | Hartman et al. | |
| 5,749,252 A * | 5/1998 | Rhoades | 70/276 |
| 5,767,402 A | 6/1998 | Sandlass et al. | |
| 5,945,607 A | 8/1999 | Peppel et al. | |
| 5,948,972 A * | 9/1999 | Samsavar et al. | 73/105 |

(Continued)

OTHER PUBLICATIONS

Abstract—publication date Sep. 13-16, 1992, pp. 454-459, vol. 1 Control Applications, 1992, First IEEE Conference, Groom, N.J., Britcher, C.P., NASA Res Ctr, Va.

(Continued)

*Primary Examiner*—Max Noori
(74) *Attorney, Agent, or Firm*—Thomas R. Kingsbury; Fay Sharpe, LLP (57) ABSTRACT

A test machine for testing the physical properties of a test specimen is provided. The test machine includes a fixture that applies a first force on the test specimen in a first direction and utilizes magnetic force to bring about the rotation of a fixture to apply a second force on the test specimen in a second direction. The test machine can better simulate field applications where a material may experience, for example compression or tension at the same time it experiences a rotational moment.

28 Claims, 6 Drawing Sheets

U.S. PATENT DOCUMENTS

| | | | |
|---|---|---|---|
| 6,058,784 | A | 5/2000 | Carroll et al. |
| 6,089,101 | A | 7/2000 | Ishii et al. |
| 6,289,744 | B1 | 9/2001 | Larson et al. |
| 6,389,876 | B1 | 5/2002 | Tanimura et al. |
| 6,405,599 | B1 | 6/2002 | Patt |
| 6,508,132 | B1 | 1/2003 | Lohr et al. |
| 6,526,837 | B1 | 3/2003 | Grote et al. |
| 6,591,690 | B1 | 7/2003 | Crockford |
| 6,609,407 | B1 * | 8/2003 | Tambini .................... 73/1.11 |
| 6,641,067 | B2 | 11/2003 | Nakazato |
| 6,679,124 | B2 | 1/2004 | Oliver |
| 6,732,591 | B2 | 5/2004 | Miles et al. |
| 6,844,721 | B2 | 1/2005 | Oliver |
| 6,868,738 | B2 | 3/2005 | Moscrip et al. |
| 6,938,494 | B2 | 9/2005 | Takada et al. |
| 6,993,410 | B2 | 1/2006 | Esterling |
| 7,002,339 | B2 | 2/2006 | Kawashima et al. |
| 7,078,839 | B2 * | 7/2006 | Kim ......................... 310/90.5 |
| 7,123,450 | B1 | 10/2006 | Villiard et al. |
| 7,193,758 | B2 * | 3/2007 | Wiklof et al. ............... 359/212 |
| 2002/0017146 | A1 | 2/2002 | Oliver |
| 2004/0020306 | A1 | 2/2004 | Moscrip et al. |
| 2004/0079166 | A1 | 4/2004 | Moscrip et al. |
| 2007/0151337 | A1 | 7/2007 | Cochran |
| 2008/0253031 | A1 | 10/2008 | Yeakley et al. |

OTHER PUBLICATIONS

Article, Material Testing Systems Optimized by the Use of Moving Magnet Linear Motors, Kirk Biegler, Endura TEC Systems, Corp.
Office Action issued Nov. 21, 2008 for U.S. Appl. No. 11/681,216.

* cited by examiner

ELECTROMAGNETIC ROTATION AND STABILITY APPARATUS

BACKGROUND

The present exemplary embodiment relates to a material testing apparatus and method capable of applying loads to a test specimen. More particularly, the present exemplary embodiment relates to a testing apparatus and method that utilizes a magnetic force to rotate a test specimen while a load is applied to the specimen. However, it is to be appreciated that the present exemplary embodiment is also amenable to other like applications.

The present material testing apparatus and method relates to the testing of elastomeric materials. Elastomeric materials may be tested for various properties. Examples of some of the properties of interest of these materials include tensile strength, hardness, compression, rebound, shear, elongation, hysteresis, etc. Unfortunately, in most cases, the evaluation of a specimen's characteristics of a particular property must be completed in isolation from other forces. This limits the usefulness of such product testing to approximate real field data for the reason that in most field applications of an elastomeric product it is difficult, if not impossible, to limit the forces being applied to an object to just one force which is applied in only one direction.

Therefore, it would be advantageous for a testing apparatus to be able to apply a predetermined amount of forces on a test specimen from selected directions at the same time or at relative proximity in time to simulate the field environment which the specimen would experience.

BRIEF DESCRIPTION

A test machine for testing a test specimen is provided. The test machine includes a fixture for contacting the specimen and applying a force to the specimen along at least one of an x-axis, y-axis, or z-axis of the test machine. At least one electromagnet for producing the at least one electromagnet being positioned such that the magnetic force produced by the at least one electromagnet is of sufficient strength and direction to cause rotation of the fixture.

A method of testing the effects of applying a rotational moment to a test specimen is also provided. The method includes applying an axial force to the test specimen along an axis. The method also includes generating a predetermined non-mechanical rotational force to thereby twist the test specimen around the axis.

DETAILED DESCRIPTION

To test for shear, tensile or compressive characteristics of an elastomeric material, a force is typically applied to a sample or test specimen of the material in a single direction, however in order to get a more accurate prediction of how the material will perform under real world conditions, it may be desirable to apply a force to the material in a second direction during, before or after the application of the force in the first direction. For example, as a tread block of a tire comes in contact with a roadway, the tread block may experience a compressive force in a first direction. While in contact with the roadway, the same tread block may also encounter a torquing force in a second direction. The inventor has developed an apparatus and a method to apply multiple forces to an elastomeric material during testing. For example, the apparatus and method can initiate a rotational torquing force on a test specimen while applying a first compressive force to the test specimen. Alternatively, the specimen may experience the rotational moment either immediately prior to or immediately after the first force. Advantageously, when applying the second force, the method does not interfere with the ability of the apparatus to apply the first force on the test specimen. Additionally, it is preferred that the method does not mechanically engage the fixture or the test specimen. Mechanically engaged is used herein to describe at least the situation when the two items would come in physical contact.

Non-limiting examples of mechanical testing equipment to which the present apparatus may be applicable are described in the following U.S. patents, which are incorporated herein by reference, in their entirety: U.S. Pat. Nos. 4,478,086, 4,869,112, 5,005,424, 5,361,640, 5,425,276, 5,693,890, 5,719,339, 6,058,784, 6,526,837, and 6,679,124. A commercially available example of such an apparatus is the MTS 831 available from MTS Systems Corporation of Eden Prairie, Minn.

Figure 1:
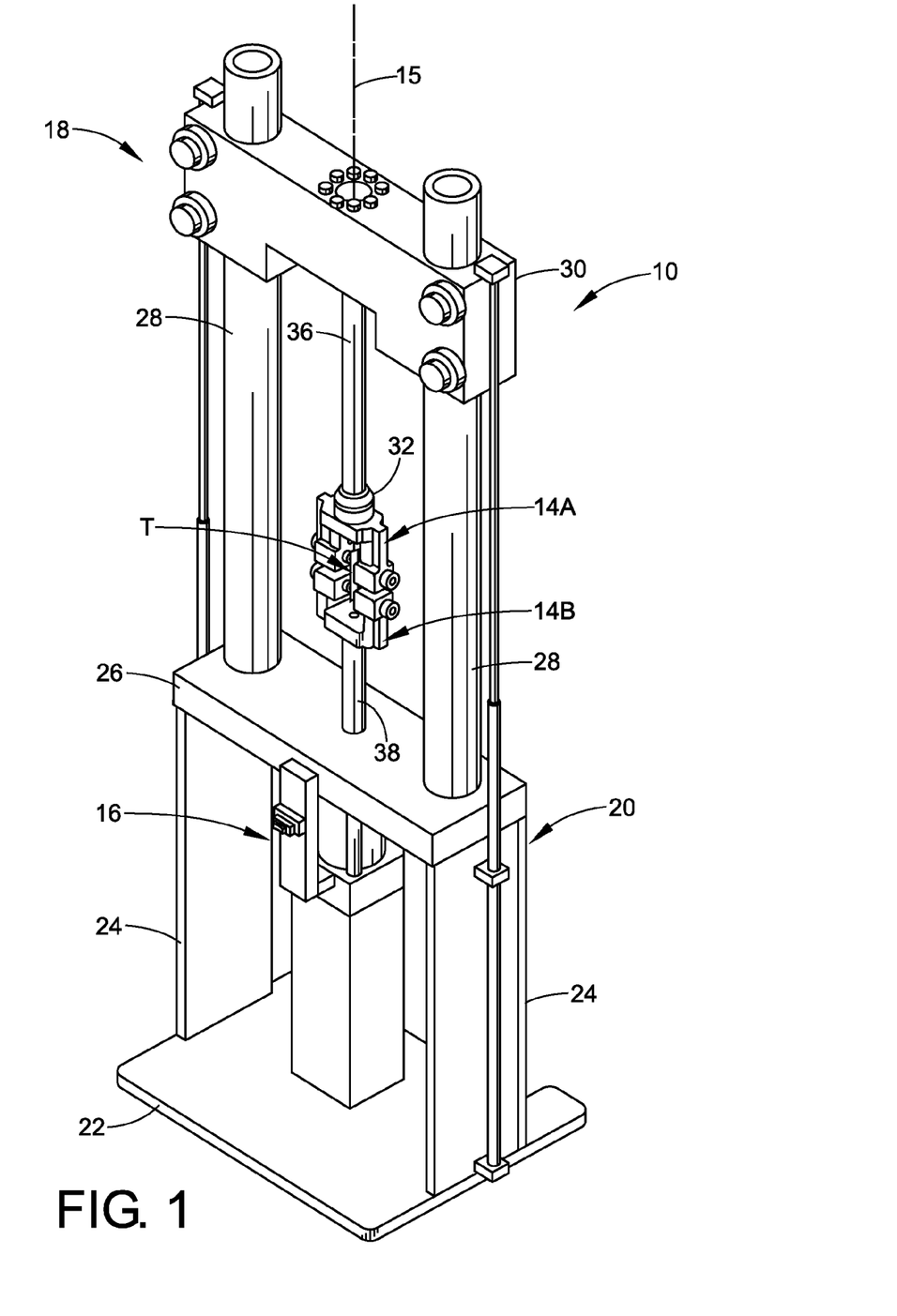
FIG. 1 is a perspective view of a material testing machine.

With respect to the first force, in FIG. 1, the invention is illustrated with an apparatus for applying a compressive or tensile force to the test specimen. This is not meant to limit the invention to only an apparatus which may apply a force to the test specimen along the vertical axis of the test specimen.

FIG. 1 illustrates an exemplary material testing apparatus 10 for applying loads to a test specimen. The apparatus 10 includes an upper fixture 14A and a lower fixture 14B that hold the test specimen (T) along a longitudinal axis 15. The lower fixture 14B is connected to an actuator 16 through which loads are applied to the test specimen (T) and reacted against a reaction structure generally indicated at 18. Optionally, the apparatus 10 may include more than one actuator. For example, a second actuator may be located proximate of fixture 14B. Alternatively, fixtures 14A and 14B may be capable of retaining the test specimen for either tensile or compressive testing.

In the embodiment illustrated, the material testing apparatus 10 includes a frame 20 having a base 22. A pair of support members 24 extends upwardly from the base 22 and is joined together by a crossbeam 26, which provides a stable support surface. A pair of stationary support columns 28 extends upwardly from the crossbeam 26 to an adjustable crosshead 30. A fixed support 36 extends from crossbeam 30 to a load cell 32. Load cell 32 joins the upper fixture 14A to support 36 and crosshead 30. The load cell 32 provides a representative signal indicative of tension/compressive forces applied to test specimen. Alternatively, the load cell may be located in communication with fixture 14B (not shown) instead of fixture 14A, as shown. A further alternative is that apparatus 10 may include more than one load cell. In one of the various embodiments of apparatus 10, the actuator or actuators are aligned with an upper or lower fixture and that the load cell or load cells are aligned with the fixture which the actuator is not aligned.

Apparatus 10 further includes an actuator 16. Actuator 16 may be powered by any type of drive system such as an electrical system, a pneumatic system, or a hydraulic system. Support 38 extends from actuator 16 to lower fixture 14B. Preferably actuator 16 is in communication with fixture 14B and actuator 16 may be used to move fixture 14B to apply a tensile force or compressive force to a test specimen.

As appreciated by those skilled in the art, the upper fixture 14A and lower fixture 14B, of apparatus 10 can take many forms and are not limited to fixtures 14A and 14B illustrated in FIG. 1. Any suitable fixture may be used to practice the invention. Examples of other such fixtures are illustrated in the aforementioned U.S. patents. The fixture is able to retain a portion of the test specimen (T) during the desired testing.

Optionally apparatus 10 may include a control system that provides control signals along a signal line to the actuator 16 (or actuators if the system includes more than one actuator) and receives signals along a control line from load cell 32 which are proportional to the forces measured by the load cell (or load cells if the system includes more than one load cell.) Examples of suitable commercially available control systems are the various FLEXTEST® control systems available from MTS Systems Corporation. FLEXTEST is a registered trademark of MTS Systems Corporation.

With respect to the apparatus 10, just as it is advantageous to displace the test specimen (T) in a desired tensile state or compressed state; it is also advantageous to be able to apply a torque to the test specimen (T) as part of the tensile or compression testing. Such a rotational moment may be applied to the test specimen prior to, during, or after the application of the first force. It would further be advantageous that the rotation is performed to a predetermined degree and at a predetermined rate.

Figure 2:
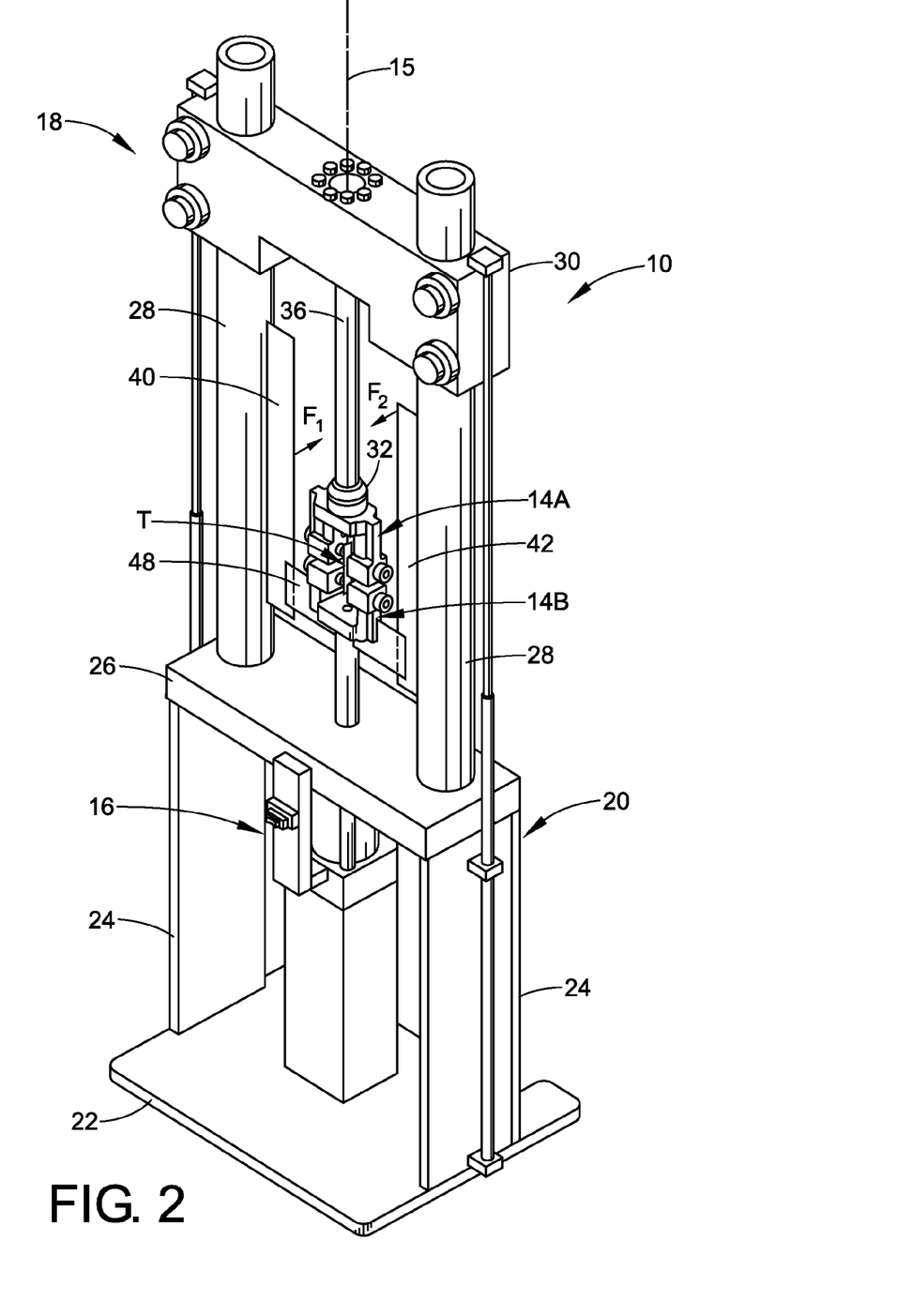
FIG. 2 is a perspective view of a material testing machine which includes an embodiment of the present material testing apparatus.

FIG. 2 shows one embodiment of the material testing apparatus. The apparatus 10 includes one or more electromagnets 40 and 42. The embodiment of FIG. 2 includes one electromagnet each on each support column 28 with electromagnets 40 and 42 extending along support columns 28 at least a distance of the displacement of fixture 14B. As shown, fixture 14B is capable of rotating and is not fixed. Various techniques may be used to allow fixture 14B to rotate. In one embodiment actuator 16 may rotate and, in turn, the rotation of actuator 16 may thereby bring about the rotation of fixture 14B. In another embodiment, support 38 may include a rotational joint, such as, but not limited to, a ball joint. In a further embodiment, the rotational joint may be integral to fixture 14B or separate from fixture 14B and support 38. The invention is not limited to the aforementioned techniques to bring about the rotation of fixture 14B.

As illustrated, magnets 40 and 42 are arranged in a "push-pull" arrangement. Push-pull is used herein to describe a pair a magnets which the magnetic forces exerted by each magnet is exerted along the same axis, be it the x, y, or z-axis; however the forces are exerted in opposite directions along the chosen axis. Therefore, the magnets are aligned to rotate the test specimen (T) in the fixture by applying its forces in opposite directions. The magnetic forces are applied to structure 48, which is attached to fixture 14B. Structure 48 is made of a material capable of reacting to a magnetic force. Examples of such a material include metallic compounds such as, but not limited to, steel, iron, and alloys of each. As illustrated, the magnetic force of magnet 40 is directed in the direction of arrow $F_1$ and the magnetic force of magnet 42 is directed in the direction of arrow $F_2$. Any known technique to power magnets 40 and 42 may used to supply power to magnets 40 and 42, to generate the magnetic force, such as applying a current to the magnets to generate the magnetic force.

With respect to magnets 40 and 42, they may have the same strength or different strengths. Also, the embodiment may include more than two (2) magnets. The magnets may be present in pairs, such as one (1), two (2), and three (3) or more pairs of magnets. However it is not to be implied that an odd number of magnets may not be used.

Furthermore, the magnets do not need to have a uniform size. The size of any two particular magnets may vary. In one particular embodiment, the heights of the magnets may be adjusted to alter the angle of rotation of the test specimen. Also, it is not required that the magnets are straight up and down as one or more of the magnets may be aligned at an angle relative to columns 28. Additionally, the current provided to each magnet does not have to be uniform. Another optional aspect of the invention is that amplification may be used to alter the signal to the magnet and to control the size of the magnetic force exerted by the magnet. In this way, the amplification is ultimately being used to control the degree of rotation. In one embodiment, the degree of rotation is a function of the vertical displacement of fixture 14B. The degree of rotation may be measured by any type of angle sensor. Amplification is not limited to just controlling the degree of rotation. In alternate embodiments, amplification may be used to control other aspects of the testing to be preformed by apparatus 10.

Figure 3:
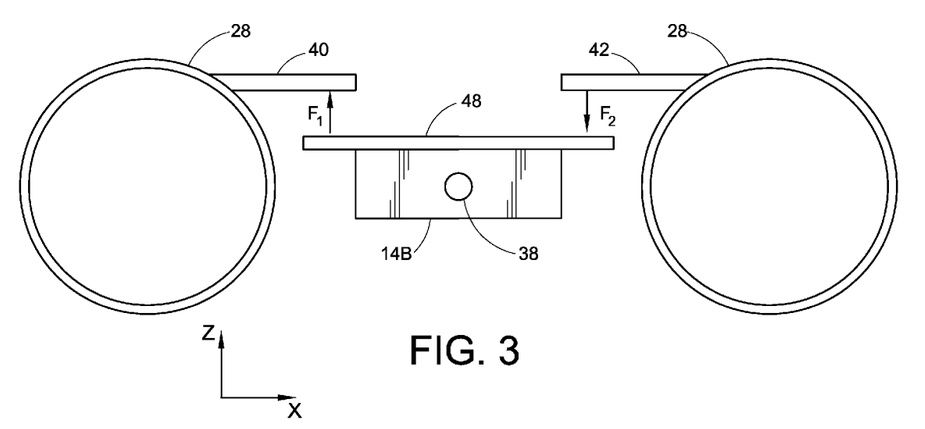
FIG. 3 is a top view of the relationship of the electromagnets in one embodiment of the material testing apparatus.

FIG. 3 shows a top view of the embodiment shown in FIG. 2. Electromagnets 40 and 42 are located on each support column 28 respectively. Preferably electromagnets 40 and 42 extend along support columns 28 at least a distance of the displacement of fixture 14B. As illustrated, magnets 40 and 42 are arranged in a "push-pull" arrangement. Therefore, the magnets are aligned to rotate the test specimen in the fixture by applying their forces in opposite directions. The magnetic forces are applied to structure 48, which is attached to fixture 14B. Structure 48 is made of a material capable of reacting to a magnetic force. As illustrated, the magnetic force of magnet 40 is directed in the direction of arrow $F_1$ and the magnetic force of magnet 42 is directed in the direction of arrow $F_2$.

Figure 4:
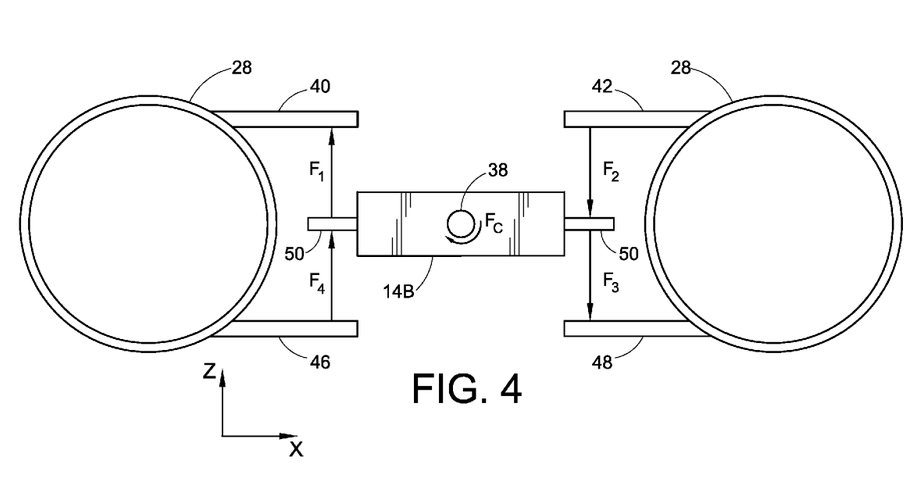
FIG. 4 is a top view of the relationship of the electromagnets in another embodiment of the material testing apparatus.

FIG. 4 shows a top view of an alternative embodiment. Electromagnets 40 and 46 are located on one support column 28, and electromagnets 42 and 44 are located on the other support column 28. Preferably electromagnets 40, 42, 44, and 46 extend along support columns 28 at least a distance of the displacement of fixture 14B. Magnets 50 are attached to fixture 14B such that they interact with electromagnets 40, 42, 44, and 46. As illustrated, diagonally opposed electromagnets 42 and 46 are arranged to push magnets 50, and diagonally opposed electromagnets 40 and 44 are arranged to pull magnets 50. Therefore, the electromagnets are aligned to rotate the test specimen in the fixture by applying their forces to magnets 50. As illustrated, the magnetic force of electromagnet 40 is directed in the direction of arrow $F_1$, the magnetic force of electromagnet 42 is directed in the direction of arrow $F_2$, the magnetic force of electromagnet 44 is directed in the direction of arrow $F_3$, and the magnetic force of electromagnet 46 is directed in the direction of arrow $F_4$ thus creating a circular torquing force or rotational moment $F_c$ on fixture 14B during, before or after the application of a compressive or other directional force applied to the test specimen by apparatus 10.

Figure 5:
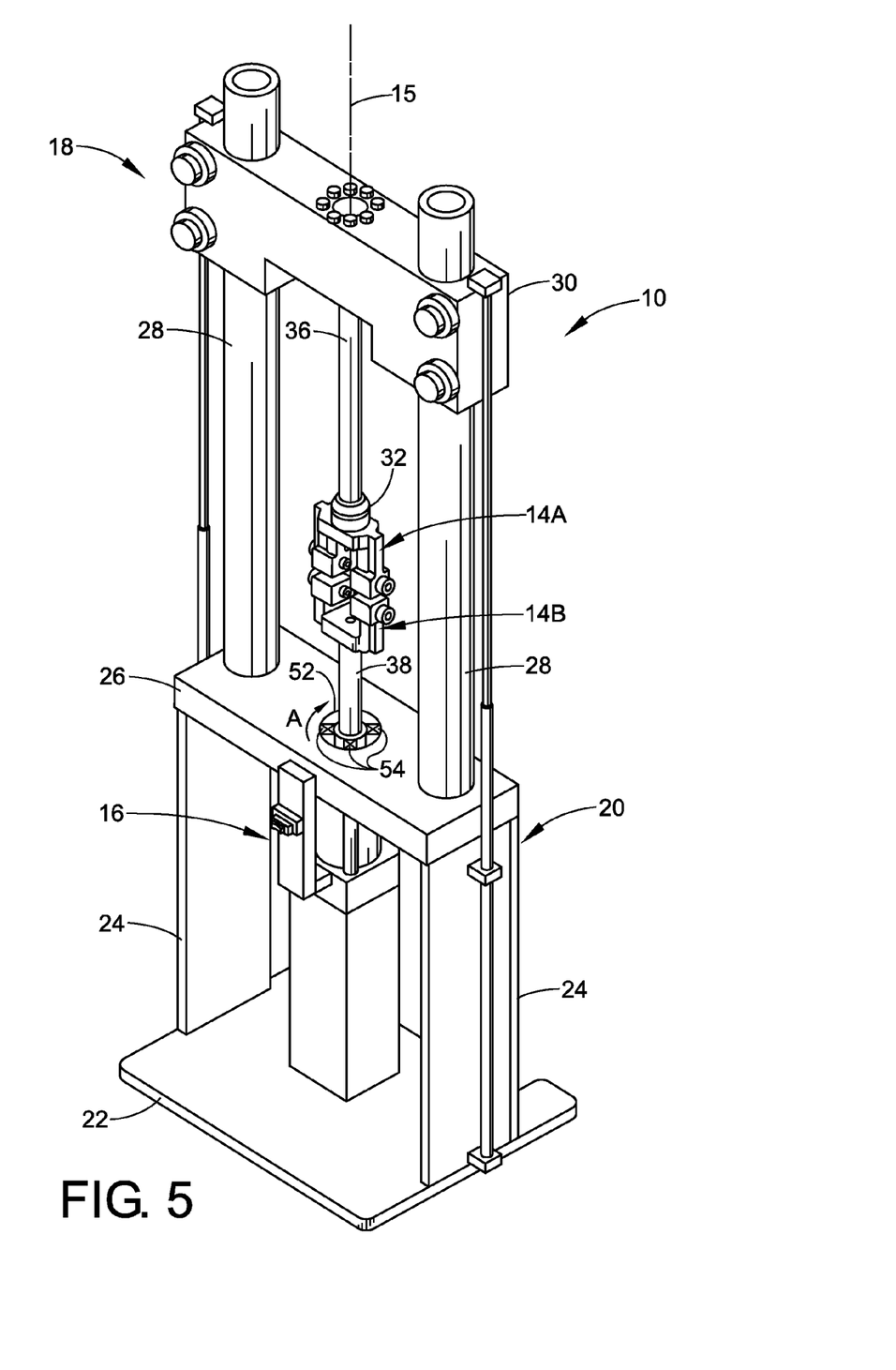
FIG. 5 is a perspective view of a material testing machine which includes another embodiment of the present material testing apparatus.

With reference to FIG. 5, a third embodiment of the invention is illustrated. In this embodiment, an electromagnetic motor is incorporated into the testing machine. In this embodiment, support 38 extends from actuator 16, through crossbeam 26 to fixture 14B in a manner that will allow support 38 to rotate. Electromagnetic motor 52 is located near one end of support 38. The motor includes a plurality of electromagnets 54. Upon the application of an electrical current to motor 52, magnets 54 produce a magnetic field in the direction of arrow A of sufficient strength to cause support 38 to rotate and thereby rotate fixture 14B.

Figure 6:
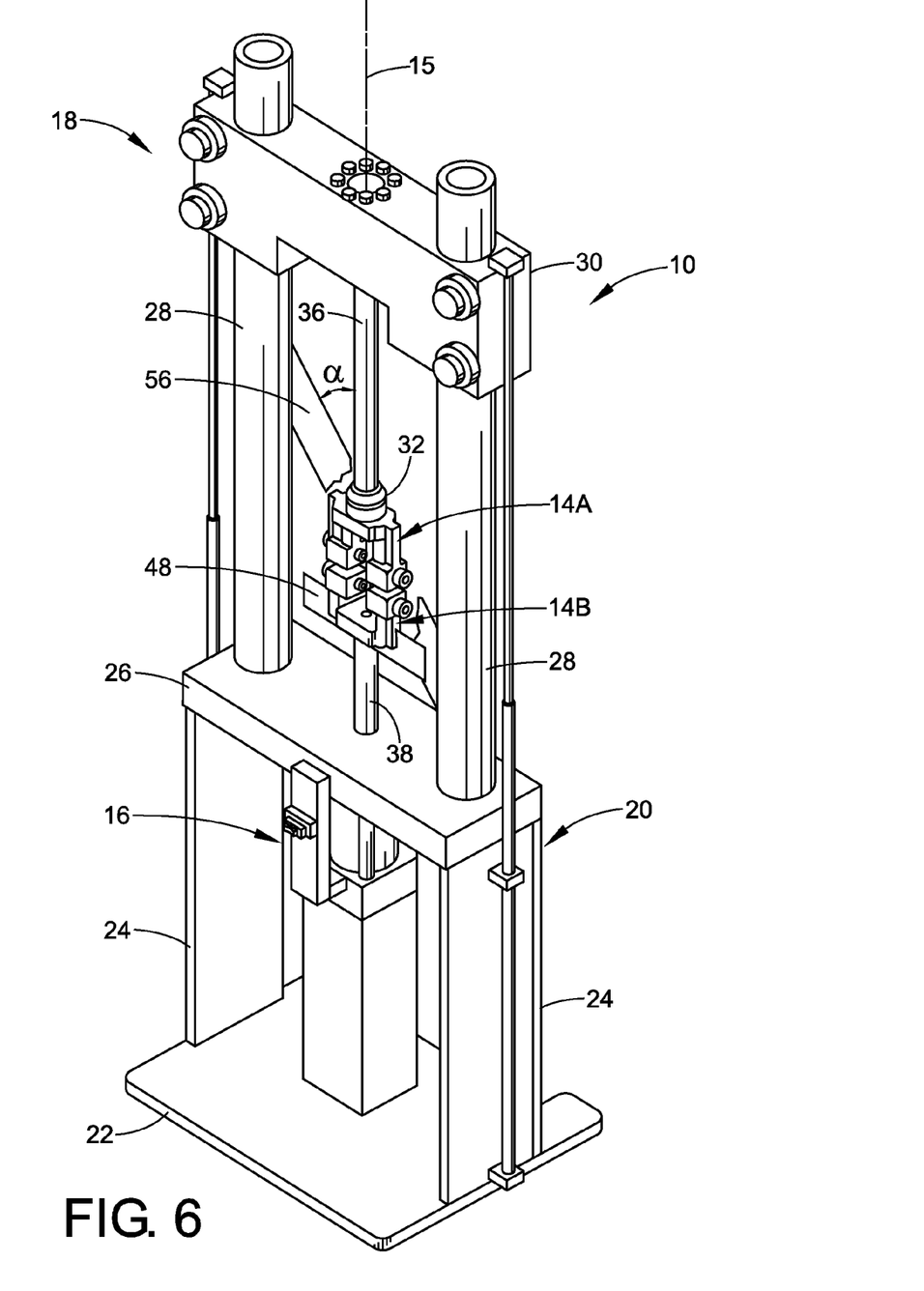
FIG. 6 is a perspective view of a material testing machine which includes a further embodiment of the present material testing apparatus.

FIG. 6 illustrates a fourth embodiment of the invention. In this embodiment, magnet 56 is attached to support columns 28 and is oriented diagonally between support columns 28. Magnet 56 can be either a permanent magnet or an electromagnet. Structure 48 is attached to test fixture 14B. Structure 48 is made of a material capable of reacting to the magnetic force exerted by magnet 56. As fixture 14B is moved along axis 15, the magnetic force is exerted onto structure 48 at localized points, i.e. the place on structure 48 that is the closest to magnet. Thus, as fixture 14B is moved along axis 15, the localized magnetic force exerted on structure 48 moves along structure 48 in a perpendicular relationship to axis 15. This causes fixture 14B to rotate as it is moved along axis 15, which in turn causes the test specimen to rotate. Angle α may be modified to change the rate of rotation relative to the amount of displacement of fixture 14B. A smaller angle α will create a very low rate of rotation relative to the amount of displacement of fixture 14B, while a larger angle α will create a large rate of rotation relative to the amount of displacement of fixture 14B. One advantage of this embodiment is that it allows for modification of the rate of rotation without the need to change amplification of an electromagnet as a function of the linear displacement of fixture 14B.

Optionally, a thickness monitor such as a laser may be added to the testing machine to determine how the thickness of the test specimen is changing as the various forces are applied to the test specimen. The above alternate/optional embodiments of the invention may be practiced in any combination thereof.

The invention also includes a method of testing the effects of applying a rotational moment to a test specimen. The method includes the step of securing at least one end of the test specimen in a fixture. In one embodiment, the test specimen is held securely enough that the desired test may be accomplished on the test specimen, but not so rigidly that the retention of the test sample interferes with the testing. In various embodiments, two opposing ends of the test specimen will be secured.

Preferably, the fixture includes a rotatable element at an end of the fixture attached to one of the opposing ends of the test specimen. The method also includes the step of applying a force to the test specimen along one of x-axis, y-axis, or z-axis of the test specimen. A predetermined non-mechanical rotational moment is applied to thereby rotate the fixture, and twist the test specimen.

Optionally the method may include the step of monitoring the twisting of the test specimen. Furthermore, the method may include adjusting the non-mechanical rotational force in response to the monitoring. Another optional step may be adjusting the linear force applied to the specimen in response to the monitoring.

The description has been provided with reference to exemplary embodiments of the electromagnetic rotation and stability apparatus. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. A test machine for testing a specimen comprising:
   a. an upper fixture and a lower fixture for contacting the specimen, said fixtures applying a force to the test specimen along at least one of an x-axis, y-axis or z-axis of the test machine;
   b. at least one electromagnet for producing a magnetic force, said at least one electromagnet being positioned such that the magnetic force produced by the at least one electromagnet is of sufficient strength and direction to cause rotation of at least one of the fixtures.

2. The test machine of claim 1 wherein the at least one electromagnet rotates the at least one fixture in a predetermined direction and at a predetermined rate of rotation.

3. The test machine of claim 1 wherein the at least one electromagnet rotates the at least one fixture along at least one of the x-axis, y-axis or z-axis of the test machine.

4. The test machine of claim 1 further comprising a pair of electromagnets.

5. The test machine of claim 4 wherein the pair of electromagnets are aligned in a push-pull configuration.

6. The test machine of claim 1 further comprising a pair of electromagnets aligned to rotate the at least one fixture in either a clock-wise direction or a counter-clockwise direction.

7. The test machine of claim 1 further comprising a pair of electromagnets aligned circumferential to one end of the at least one fixture and within a proximity of the end to thereby generate the magnetic force to rotate the at least one fixture.

8. The test machine of claim 1 further comprising a load cell in communication with at least one of the fixtures and capable of measuring a load applied to the test specimen.

9. A test machine comprising:
   a. a fixture that contacts a test specimen; and
   b. a non-mechanical force element aligned to apply a rotational moment of a predetermined magnitude to thereby rotate the fixture, the force element comprising at least one pair of electromagnets that are aligned in a push pull configuration.

10. A test machine for testing a test specimen, comprising:
    a. a structure;
    b. a fixture attached to the structure that contacts the test specimen, the fixture being movable to apply a tensile force or a compressive force along an axis to the test specimen; and
    c. a magnet positioned to apply a predetermined magnetic force on the fixture, wherein the magnetic force is of sufficient strength and direction to rotate the fixture about the axis.

11. The test machine of claim 10, wherein the magnet is positioned diagonally in relation to a fixed support, such that the magnet is at an angle of less than 90 degrees in relation to the fixed support.

12. The test machine of claim 11, wherein the magnet is adjustable on the structure.

13. A method of testing the effects of applying a rotational moment to a test specimen comprising
    a. applying an axial force to the test specimen along an axis; and
    b. generating a predetermined non-mechanical rotational force to thereby twist the test specimen around the axis.

14. The method of claim 13 further comprises monitoring the twisting of the test specimen.

15. The method of claim 13 further comprises adjusting the non-mechanical rotational force in response to the monitoring.

16. The method of claim 13 further comprises adjusting the axial force in response to the monitoring.

17. The method of claim 13 further comprising adjusting the axial force and adjusting the non-mechanical rotational force.

18. The method of claim 13 wherein the non-mechanical rotational force comprises a magnetic force.

19. The method of claim 13 wherein the applying the axial force comprises applying a tensile force to the test specimen.

20. The method of claim 13 wherein the applying the axial force comprises applying a shear force to the test specimen.

21. The method of claim 13 wherein the applying the axial force comprises applying a compressive force to the test specimen.

22. A test machine for testing the physical properties of a test specimen having a base, a test fixture mounted on the base for engaging the test specimen, said test fixture applying a force to the test specimen in a first direction, the improvement comprising:
at least one electromagnet for generating a magnetic force, said magnet being positioned such that the magnetic force rotates the test fixture in a second direction.

23. The test machine of claim 22 wherein the second direction comprises around an axis of the first direction.

24. The test method of claim 22 wherein the at least one electromagnet comprises a pair of electromagnets.

25. The test machine of claim 24 wherein the pair of electromagnets aligned in push-pull configuration.

26. The test machine of claim 10 wherein the fixture includes an upper fixture and a lower fixture.

27. The test machine of claim 26 wherein the lower fixture moves along the axis and rotates about the axis.

28. The test machine of claim 9, wherein the fixture moves along the axis.

* * * * *